United States Patent
Ptchelintsev

[11] Patent Number: 5,951,990
[45] Date of Patent: *Sep. 14, 1999

[54] ASCORBYL-PHOSPHORYL-CHOLESTEROL

[75] Inventor: Dmitri S. Ptchelintsev, Mahwah, N.J.

[73] Assignee: Avon Products, Inc., New York, N.Y.

[*] Notice: This patent is subject to a terminal disclaimer.

[21] Appl. No.: 08/853,271

[22] Filed: May 9, 1997

Related U.S. Application Data

[63] Continuation-in-part of application No. 08/440,765, May 15, 1995, abandoned.

[51] Int. Cl.$^6$ ............................... A61K 7/00; A61K 7/06
[52] U.S. Cl. .................... 424/401; 424/59; 424/60; 424/70.1; 424/70.2; 424/641; 424/642; 424/617; 424/703; 514/169; 514/171; 514/474; 514/844; 514/880
[58] Field of Search ............................... 424/401, 59, 60, 424/70.1, 70.2, 641, 642, 617, 703; 514/474, 169, 171, 880, 844

[56] References Cited

U.S. PATENT DOCUMENTS

| | | |
|---|---|---|
| 3,151,127 | 9/1964 | Spanel . |
| 4,564,686 | 1/1986 | Ogata ........................ 549/220 |
| 4,939,128 | 7/1990 | Kato et al. .................. 514/82 |
| 4,954,532 | 9/1990 | Elliott et al. . |
| 5,306,713 | 4/1994 | Suetsugu et al. ........... 514/100 |
| 5,336,485 | 8/1994 | Fariss ........................ 424/10 |
| 5,508,275 | 4/1996 | Weithmann et al. ....... 514/182 |

FOREIGN PATENT DOCUMENTS 92104149 9/1992 United Kingdom .

OTHER PUBLICATIONS

Menon et al., *Structural Basis for the Barrier Abnormality Following Inhibition of HMG CoA Reductase in Murine Epidermis*, J. Invest. Dermatol., vol. 98, pp. 209–219 (1992).

Steinhart et al., *Pro–and Antioxidative Effect of Ascorbic Acid on L–Tryptophan in the System $FE^{3+}$/ Ascorbic Acid/ $O_2$*, J. Agric. Food Chem., vol. 41, pp. 2275–2277 (1993).

Sakamoto et al., *Measurement Method of Efficacy of Anti-dandruff Cosmetics and Development of the New Active Commerical Product*, IFSCC, Yokohama, Vol. B206, pp. 823–864 (1993.

*Primary Examiner*—Gollamudi S. Kishore
*Attorney, Agent, or Firm*—Ohlandt, Greeley, Ruggiero & Perle, L.L.P.

[57] ABSTRACT

This disclosure relates to a derivative of L-ascorbic acid which is stable, easily incorporated into cosmetically acceptable vehicles and enzymatically bioreversible in the skin to free ascorbic acid and a safe alkanol component. The L-ascorbic acid derivative includes cholesterol. The L-ascorbic acid derivative is a compound selected from the group consisting of 3'-(L-ascorbyl-2-o-phosphoryl)-cholesterol, isomers thereof and salts thereof.

39 Claims, 1 Drawing Sheet

ASCORBYL-PHOSPHORYL-CHOLESTEROL

RELATED APPLICATION

This application is a continuation-in-part of application Ser. No. 08/440,765, filed May 15, 1995, now abandoned.

BACKGROUND OF THE INVENTION

I. Field of the Invention

The present invention relates to the synthesis and use of a novel derivative of L-ascorbic acid. This derivative of L-ascorbic acid includes cholesterol. The resultant product is stable, easily incorporated into cosmetically acceptable vehicles and enzymatically bioreversible.

II. Description of the Prior Art

The use of L-ascorbic acid as an antioxidant in food preparations is known. For example, Steinhart, *Pro- and Antioxidative Effect of Ascorbic Acid on L-Tryptophan in the Fe3+/Ascorbic Acid/O*, J. Agric. Food Chem., Vol. 41, pages 2275–2277 (1993) describes the use of L-ascorbic acid as an antioxidant in food to remove free radicals and undergoing rapid oxidation.

Similarly, free L-ascorbic acid in topical preparations demonstrates poor stability and tends to break down due to partially oxidative and non-oxidative degradation. The degraded ascorbic acid loses activity and the resultant product loses aesthetic appeal since it exhibits a cosmetically undesired brown color.

While cholesterol is considered unhealthy especially when ingested, the benefits of cholesterol, necessitated with L-ascorbic acid, for skin barrier repair are known. For example, Menon, *Structural Basis for the Barrier Abnormality Following Inhabitations of HMG CoA Reductase in Murine* Epidermis, J. Invest. Dermatol., Vol. 98, pages 209–219 (1992), describes deficiencies in the skin barrier repair mechanism when cholesterol synthesis is inhibited by regulation of HMG CoA reductase.

Presently, mechanical mixing of L-ascorbic acid and cholesterol results in an unstable product due to the instability of L-ascorbic acid. For example, U.S. Pat. No. 4,939,128 to Kato is directed to the use of phosphoric acid esters of ascorbic acid for the treatment of diseases, not for cosmetics, topical dermatological or skin uses, and teaches that certain phosphoric acid esters of ascorbic acid display improved oxygen scavenging properties. One of the phosphoric acid esters in the patent is substituted with a cholestanyl group. The conspicuous absence of cholesterol and the specific mention of a cholesteryl group recognizes that conjugates of L-ascorbic acid and cholesterol were then not practical or desired.

Attempts have been made to conjugate ascorbic acid with a glycyrrhetic group as described in European Application No. 92104149.7; and with a tocopheryl group as indicated by U.S. Pat. No. 3,151,127. U.S. Pat. Nos. 4,564,686 and 5,306,713 disclose tocopheryl ascorbyl phosphate as an anti-oxidant having the following structure:

Also, Sakamoto, *Measurement Method of Efficacy of Antidandruff Cosmetics and Development of the New Active Commercial Product*, IFSCC, Yokohama, Vol. B206, pages 823–864 (1993) describes the use of tocopheryl coupled to L-ascorbic acid. The coupled tocopheryl is an antioxidant preservative for the ascorbyl group, but the use of the ascorbyl-tocopheryl as a skin therapeutic is questionable since, unlike cholesterol, tocopheryl is not a natural substrate for the skin.

Heretofore, there has been needed a stable product having cholesterol coupled to L-ascorbic acid, which product retained full functional activity even after decoupling by naturally occurring acidic phosphatases in the skin. This product would provide the beneficial properties of L-ascorbic acid, including increased collagen production and skin-lightening, combined with the benefits of released cholesterol, namely improved elasticity, resistance, tone and moisture retention of the skin. Accordingly, there has been needed a method for covalently and bioreversibly effecting the coupling of cholesterol to L-ascorbic acid.

SUMMARY OF THE INVENTION

It is an object of the present invention such a stable composition that is a novel derivative of L-ascorbic acid that includes cholesterol.

It is another object of the present invention to provide to provide such a stable composition of cholesterol coupled to L-ascorbic acid for use in cosmetic products.

It is still another object of the present invention is to provide such a stable composition having multiple skin care benefits.

It is a further object of the present invention is to provide such a stable composition that is easily carried in cosmetic vehicles, enzymatically bioreversible, and demonstrates extended shelf-life.

It is yet a further object of the present invention is to provide a method for covalently and bioreversibly coupling cholesterol to L-ascorbic acid for stabilization of the resulting molecule.

To accomplish the forgoing objects and advantages, the present invention, in brief summary, is a derivative of L-ascorbic acid that includes cholesterol. Such derivatives are, for example, 3'-(L-ascorbyl-2-o-phosphoryl)-cholesterol or isomers thereof and their salts thereof.

These and other objects of the present invention will become evident from the invention described below.

DETAILED DESCRIPTION OF THE PREFERRED EMBODIMENT

Figure 1:
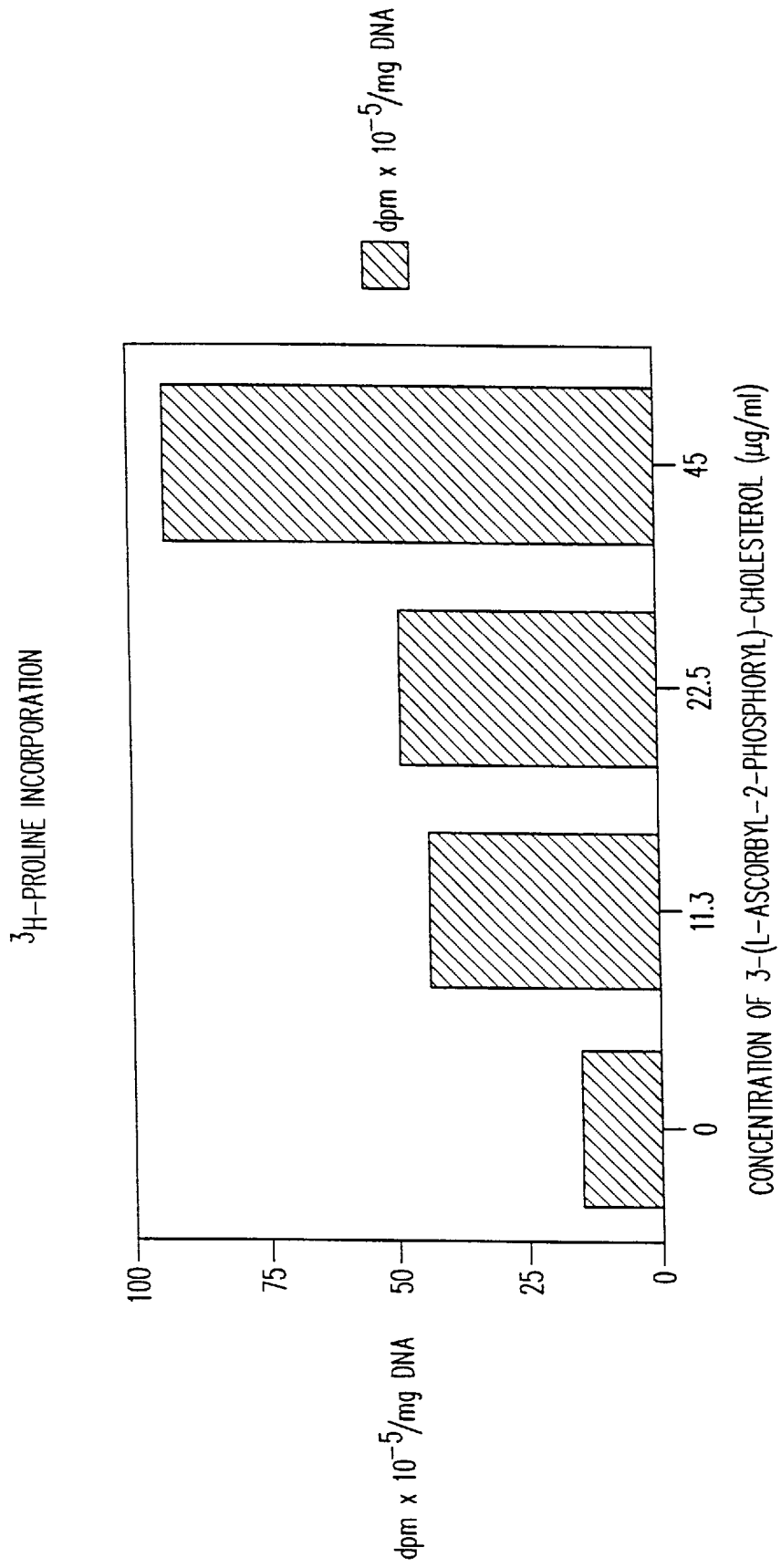
FIG. 1 illustrates that 3'-(L-ascorbyl-2-phosphoryl)-cholesterol increases production of new collagen by human fibroblasts in a dose dependent manner.

The present invention includes a novel derivative of L-ascorbic acid. The derivative is formed by a coupling of

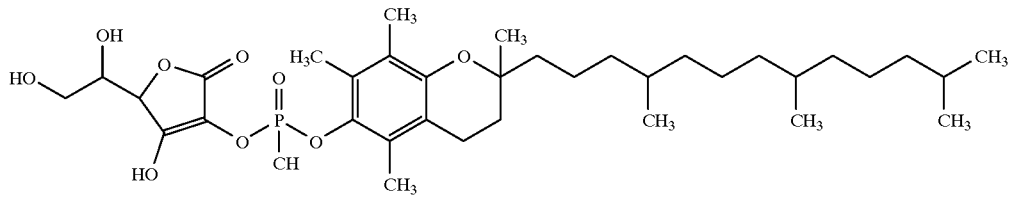

L-ascorbic acid and cholesterol. The novel derivative, that can be easily included in a suitable topical vehicle, is selected from the group consisting of 3'-(L-ascorbyl-2-o-phosphoryl)-cholesterol, 3'-(L-ascorbyl-3-o-phosphoryl)-cholesterol or isomers and their salts thereof. The exemplary compounds include isomers of 3'-(L-ascorbyl-2-o-phosphoryl)-cholesterol(Formula I) such as 3'-(L-ascorbyl-3-o-phosphoryl)-cholesterol (Formula II). Both formulas are illustrated below.

amine, such as ethanolamine, may also be used in combination with the L-ascorbic acid derivative.

Suitable vehicles include conventional lotions, creams or gels. A "physiologically acceptable vehicle" or a "suitable vehicle" means drugs, cosmetics, medicaments or inert ingredients that are suitable for use in direct contact with human tissues without undue toxicity.

A first or more basic lotion comprises about 0.10 to about 20.0 weight percent of the L-ascorbic acid derivative, and

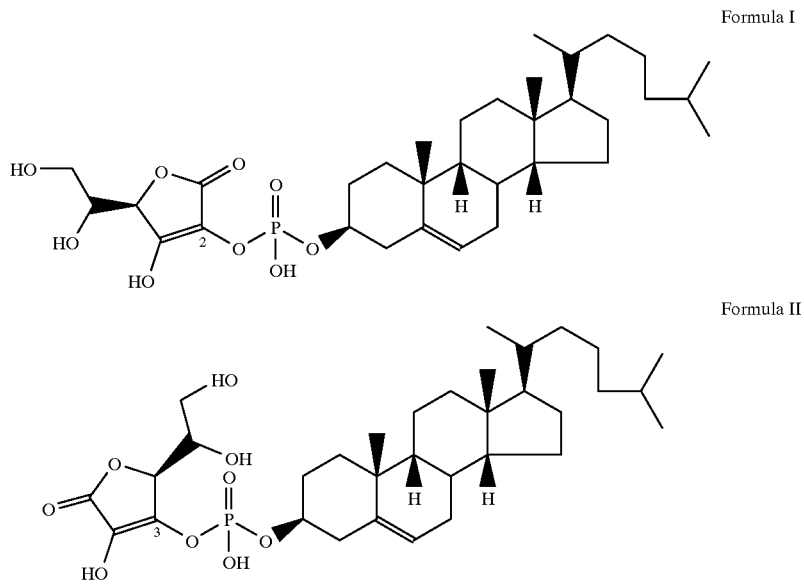

Formula I

Formula II

The L-ascorbic acid is covalently bounded to the cholesterol by phosphoryl or phosphates so that the L-ascorbic acid derivative set forth above is also called ascorbyl-phosphoryl-cholesterol.

In the ascorbyl-phosphoryl-cholesterol compounds of the present invention, the conjugated ascorbic acid becomes resistant to degradation. The cholesteryl group serves as a carrier moiety and facilitates delivery of polar ascorbic acid through the non-polar outermost protective layer of skin (i.e., the stratum corneum) and increases the bioavailability of the ascorbic acid in the topical application.

Natural enzymes, such as phosphatases present in the skin, gradually cleave the phosphoryl or phosphate linkage between cholesterol and ascorbic acid, resulting in sustained release of free L-ascorbic acid and cholesterol into the stratum corneum. The released cholesterol is a natural substrate for skin and supplements that otherwise produced by the body. Topically applied cholesterol improves elasticity, tone and resistance to drying.

The basic topical formula may comprise from about 0.0001 to about 100, with all ranges set forth in weight percent, of the L-ascorbic acid derivative. In a preferred embodiment, about 0.05 to about 50 weight percent of the L-ascorbic acid derivative is in a cosmetically acceptable vehicle. In a more preferred embodiment, about 0.10 to about 20 weight percent of the L-ascorbic acid derivative is combined with a cosmetically acceptable vehicle, and in an even more preferred embodiment about 1.0 to about 10 weight percent. Salts of the L-ascorbic acid derivative, namely ammonium, calcium, lithium, potassium or sodium can be incorporated with the L-ascorbic derivative into a cosmetically acceptable vehicle. A salt with an organic the remainder is or includes water. Most preferably, the L-ascorbic acid derivative is 3'-(L-ascorbyl-2-o-phosphoryl)-cholesterol (Formula I) or 3'-(L-ascorbyl-3-o-phosphoryl)-cholesterol (Formula II) and, preferably, the L-ascorbic acid derivative is isomers and/or salts thereof. A second lotion has about 0.10 to about 20.0 weight percent L-ascorbic acid derivative, about 0.001 to about 1.5 weight percent thickener or thickening agent, and the remainder is or includes water. The second lotion may also include up to about 1.0 weight percent fragrance.

Examples of thickening agents suitable for use with the L-ascorbic acid derivative include xanthan gum, xanthan gum brine tolerant, hydroxypropyl cellulose, hydroxyethyl cellulose, carbopol and gum acacia, polyacrylamide isoparaffin emulsion (available from Seppic Co. under the tradename SEPPIGEL 305), vee-gum or magnesium aluminum silicate or combination thereof. The thickening agent is preferably xanthene gum or hydroxyethyl cellulose or a combination thereof.

A third lotion has, besides about 0.10 to about 20.0 weight percent L-ascorbic acid derivative, about 0.50 to about 1.40 weight percent of a thickening agent, about 0.50 to about 6.0 weight percent of an emollient, about 4.8 to about 14.5 weight percent of an emulsifier, and the remainder is or includes water. It may also include about 0.35 to about 0.45 weight percent of a preservative.

In the third lotion, the thickening agent is preferably about 0.25 to about 0.70 weight percent of xanthan gum, and about 0.25 to about 0.70 weight percent of hydroxyethyl cellulose. The emollient, which can be a humectant, preferably is glycerin. The emulsifier is preferably a combination of emulsifiers, namely about 2.0 to about 8.0 weight percent of propylene glycol decapitate, about 1.8 to about 4.0 weight percent of Peg 40 Stearate, and about 1.0 to about 2.5 weight percent of Steareth-2. The preservative is preferably about 0.15 to about 0.20 weight percent of disodium EDTA or EDTA salt, and about 0.20 to about 0.25 weight percent of methylparaben.

A second cosmetic vehicle, a cream, comprises about 0.10 to about 20.0 weight percent of the L-ascorbic acid derivative, about 0.1 to about 1.20 weight percent of a thickening agent; about 0.1 to about 15 weight percent of an emulsifier, and the remainder is or includes water. It may also include up to about 1 weight percent of fragrance.

A second, less preferable, cream has about 0.5 to about 4.0 weight percent of an emollient, preferably glycerin; about 2.0 to about 6.0 weight percent of an emollient/humectant, preferably propylene glycol; emulsifiers, preferably about 1.8 to about 3.0 weight percent Steareth-20, about 0.8 to about 2.0 weight percent Steareth-2, about 1.0 to about 2.5 weight percent cetyl alcohol, and about 0.9 to about 3.5 weight percent glycerol mono-stearate; thickening agents, such as about 0.25 to about 0.6 weight percent xanthan gum and about 0.25 to about 0.6 weight percent hydroxyethyl cellulose; and a preservative, preferably about 0.15 to about 0.2 weight percent disodium EDTA or EDTA salt.

While such lotions or creams can be made by conventional homogenization methods, such lotions and creams can also be made by a process of microfluidization that involves co-mixing the aqueous phase and the oil phase of such creams and lotions in a high-pressure homogenizer that reduces the emulsion particle size dramatically to about $\frac{1}{400}$th the size of those in creams and lotions prepared without applying high pressure. Microfluidization permits the preparation of elegant stable creams and lotions containing effective amounts of the L-ascorbic acid derivative without the use of traditional emulsifiers and surfactants.

With respect to the L-ascorbic acid derivative in a gel vehicle, a first or preferred gel has about 0.10 to about 20 weight percent L-ascorbic acid derivative, about 0.30 to about 2.0 weight percent thickening agent, and the remainder includes water. A second or less preferred gel has about 0.10 to about 20.0 weight percent L-ascorbic acid derivative; about 2.0 to about 6.0 weight percent of an emollient/humectant, preferably propylene glycol; about 0.4 to about 1.5 weight percent of a thickening agent, preferably hydroxyethyl cellulose; and a preservative, preferably about 0.15 to about 0.20 weight percent disodium EDTA or EDTA salt and about 0.20 to about 0.25 weight percent methylparaben.

The pH of the lotion, cream or gel formulas can be adjusted to physiologically acceptable levels with sufficient amounts (preferably about 3.0 to about 7.5 weight percent) of ammonium hydroxide, calcium hydroxide, lithium hydroxide, potassium hydroxide, sodium hydroxide, ethanolamine, diethanolamine or urea.

As stated above, an emollient used in the above lotion, cream and gel formulas is glycerin and an emollient/humectant is propylene glycol. Besides such emollients, the L-ascorbic acid derivative or the lotion, cream or gel formulas can also be combined with most other conventional emollients, such as mineral oil, petrolatum paraffin, ceresin, ozokerite, microcrystalline wax, perhydrosqualene, dimethyl polysiloxanes, methylphenyl polysiloxanes, silicone-glycol copolymers, triglyceride esters, acetylated monoglycerides, ethoxylated glycerides, alkyl esters of fatty acids, fatty acids and alcohols, lanolin and lanolin derivatives, polyhydric alcohol esters, sterols, beeswax derivatives, polyhydric alcohols and polyethers, and amides of fatty acids. Other suitable emollients can be found in Sagarin, *Cosmetics, Science and Technology*, 2nd Ed., vol. 1, pp. 32–43 (1972), the contents of which are incorporated by reference herein.

In the above formulas, the emulsifiers can be cationic, anionic, non-ionic, amphoteric, or a combination thereof. A non-ionic emulsifier is preferred. As set forth above, the non-ionic emulsifiers propylene glycol decapitate, PEG 40 Stearate, Steareth-20, Steareth-2 and cetyl alcohol are used in various formulas. Examples of other non-ionic emulsifiers are commercially available sorbitans, alkoxylated fatty alcohols and alkyl polyglycosides. Anionic emulsifiers may include soaps, alkyl sulfates, monoalkyl and dialkyl phosphates, alkyl sulphonates and acyl isethionates. Other suitable emulsifiers can be found in McCutcheon, *Detergents and Emulsifiers*, North American Edition, pp. 317–324 (1986), the contents of which are incorporated herein by reference.

Other suitable preservatives, besides Distoma EDTA and methylparaben set forth above, include alkanols, especially ethanol and benzyl alcohol, parabens, sorbates, urea derivatives and isothiazolinones.

Suitable humectants include urea, PCA, amino acids, certain polyols and other compounds with hygroscopic properties.

The present invention includes topically applying an effective amount in a physiologically acceptable vehicle to a skin area, normally once or twice daily. The effective amount and the frequency of application will vary depending on the particular skin, the age and physical condition of the person, and like factors within the knowledge and expertise of those skilled in the art.

The L-ascorbic acid derivative in an amount about 0.05 to about 10 weight percent, and more preferably about 0.05 to about 5 weight percent, can be in topical compositions alongside keratolytic agents and skin lightening agents. The keratolytic agents may include salicylic acid and benzoyl peroxide. The skin lightening agents may include kojic acid, benzoquinone, licorice derivatives, magnesium ascorbyl phosphate, glycerhetinic acid and its derivatives.

The L-ascorbic acid derivative in an amount about 0.001 to about 25 weight percent can also be used with organic and inorganic sunscreens, such cinnamic acid derivatives (menthyl, octyl, 2-ethylhexyl, benzyl, alphaphenyl cinnamonitrile, and butyl cinnamoyl pyruvate), titanium dioxide, zinc oxide, benzylidene camphor, anthranilates, and naphtholsulphonates. The cinnamic acid derivatives are preferred.

About 0.001 to about 10 weight percent, and more preferably about 0.001 to 5 weight percent of the L-ascorbic acid derivative can be co-formulated with (a) retinoids, (b) hormonal compounds, (c) alpha-hydroxyacids or polyhydroxy alpha-hydroxy acids, or (d) alpha-keto acids.

The retinoids include, for example, retinol, retinoic acid, retinyl palmitate, retinyl propionate, retinyl acetate, isotretinoin and synthetic retinoid mimics. The hormonal compounds include, for example, estriol, estradiol, estrone or conjugated estrogens. The alpha-hydroxyacids or polyhydroxy alpha-hydroxy acids include, for example, glycolic acid, lactic acid, tartaric acid, gulonic acid and other carboxylic acids and their monomeric, polymeric, cyclic or acyclic derivatives. The alpha-keto acids include, for example, pyruvic acid, 2-oxopropanoic acid, 2-oxobutanoic acid, 2-oxopentanoic acid and the like.

The L-ascorbic acid derivative can be used for additional benefits in topical formulations that include the following ingredients: vitamins, enzyme co-actors such as vitamin B6, vitamin B12, vitamin D3, 1,25-dihydroxy vitamin D3, vitamin B1, riboflavin, vitamin K, vitamin E, tocotrienols and their derivatives, nicotinic acid and its esters, pantothenic acid and its esters, panthenol, folic acid and its derivatives, choline, carnitine and substances without formal vitamin status or "pseudo-vitamins" such as vitamin F or cis, cis-linoleic acid, vitamin M or pteroylglutamic acid, vitamins B10 and B11, sesame seed factor, termitin, penicin, insectine, hypomycin and mycoine, vitamin L or anthranilic acid, vitamin L2 or adenylthiomethyl-pentose, myoinositol or cis-1,2,3,5-trans-4-6-cyclohexanehexol and its esters, especially phytic acid, laetrile or 1-mandelo-nitrile-beta-glucuronic acid, amygdalin, vitamin B15 or pangamic acid, vitamin B13 or orotic acid, vitamin H3 or procaine hydrochloride, vitamin U or methyl-sulfonium salts of methionine and pyrroloquinoline quinone, or effective amounts of antifungal agents such as clotrimazole, ketoconazole, miconazole, naftifine, tolnaftate, amphotericin B, nystatin, 5-fluorocytosine, griseofulvin, haloprogin, of which tolnaftate, haloprogin and miconazole are most preferred. In formulas that include one or both of the preferred, the L-ascorbic acid derivative is present in an amount from about 0.001 to about 10 and, more preferably, about 0.001 to about 5 weight percent.

About 0.001 to about 20 weight percent of the L-ascorbic acid derivative can be used with one or more of:

(1) self-tanning agents, such as dihydroxyacetone and lawsone, with the former one being most preferred;

(2) anti-mycobacterial agents, such as erythromycin, tetracyclin and related compounds, especially doxycyclin and methacyclin, cephalosporine, penicillins, macrolides, peptide compounds selected from the group consisting of novobiocin, vancomycin, oleandomycin, paromomycin, leucomycine, amphomycin with macrolide molecules preferred over the polypeptide compounds, quinolone derivatives, and other compounds which interfere with bacterial cell wall synthesis, membrane function, RNA metabolism, puline, pyrimidine and protein synthesis, respiration or phosphorylation;

(3) topical analgesics, such as lidocaine, benzocaine, butamben, butacaine, tetracaine, clove oil, eugenol, with lidocaine and benzocaine being most preferred;

(4) lipidic compounds essential for the skin's barrier function such as ceramides, essential fatty acids and their esters, especially glycerides, ω-hydroxy fatty acids and their esters derived with alkanols through carboxylic hydroxyl or with other fatty acids at the omega-hydroxyl, the latter type being most preferred, with phospholipids. The lipidic compounds can be added to a topical composition either as singular molecular entities or as a complex mixture of lipids derived from either synthetic, animal or plant sources;

(5) antiallergenic agents and H1 and/or H2 antihistamines, such as diphenylhydramine, clemizole, antazoline, thenaldine, phenyltoloxamine citrate, tricyclic antiallergenics, such as ketotifene, dithiadene and 3-thienylsulfide of thiadene, H2-receptor blockers, especially burimamide, metiamide and cimetidien, cromolic acid and its salts;

(6) the L-ascorbic acid derivative can be used with topical anti-inflammatory agents that can reduce inflammation. These agents are at a concentration from about 0.001% to about 10%, preferably, about 0.5 to about 1%, with the concentration of the anti-inflammatory adjusted up or down depending upon the potency of the utilized agents. Examples of steroidal anti-inflammatories that can be used with the L-ascorbic acid derivative include hydrocortisone, hydroxytriamcilone, alpha-methyl dexamethasone, dexamethasone phosphate, beclamethasone dipropionate, hydrocortisone valerate, hydrocortisone cyclopentylpropionate, prednisolone, prednisone, and mixtures thereof, with the most preferred being prednisolone and hydrocortisone;

(7) non-steroidal anti-inflammatories can also be employed, such as described in Rainsford, *Antiinflammatory and Anti-Rheumatic Drugs*, Vols. I–III, CRC Press, Boca Raton, Fla. (1985). Specific examples of suitable non-steroidal anti-inflammatories include oxicams (e.g. piroxicam, isoxicam), fenamic acid derivatives, meclofenamic acid derivatives (e.g. sodium meclofenamate), flufenamic acid derivatives, mefenamic acid derivatives, propionic acid esters, such as ibuprofen, naproxen, benoxaprofen, flubiprofen, ketoprofen, suprofen, with ibuprofen being most preferred; pyrazolidinediones, with phenylbutazone being most preferred; the acetic acid derivatives, such as diclofenec, fenclofenac, indomethacin, sulindac, with indomethacin being most preferred; salicylic acid derivatives, such as aspirin, disalacid, benorylate, with aspirin and disalacid being most preferred.

The compositions of the present invention may also include safe anti-inflammatory products of natural origin shown to possess anti-inflammatory activity such as aloe vera extracts, extracts from genus Rubis (Rubia Cordifolio), extracts from genus Commiphom (Commiphora Mukul), Willow bark, matricarria flowers, arnica flower, comfrey root, fenugreek seed and the like known to those skilled in the art.

About 0.001 to about 20 weight percent of the L-ascorbic acid derivative can be used in formulas that contain anti-oxidants with phenolic hydroxy functions, such as gallic acid derivatives (e.g. propyl gallate), bio-flavonoids (e.g. quercetin, rutin, daidzein, genistein), ferrulic acid derivatives (e.g. ethyl ferrulate, sodium ferrulate), 6-hydroxy-2,5,7,tetra-methylchroman-2-carboxylic acid. The compositions may also contain effective concentrations of water soluble anti-oxidants such as, for example, uric acid, reductic acid, tannic acid, rosmarinic acid and catechins. Also the L-ascorbic acid derivative can be co-formulated with nitric oxide synthase inhibitors to reduce skin redness, vasodilation and inflammatory reactions, especially in response to electromagnetic and ionizing radiation or to the action of chemically or biochemically aggressive compounds. The nitric oxide synthase inhibitors can be added at concentrations from about 0.05% to about 10%, most preferably from about 1% to about 3%. The nitric oxide synthase inhibitors are selected from the group consisting of guanidine derivatives, especially monoaminoguianidine and methylguanidine, L-arginine derivatives, especially $N^G$-nitro-L-arginine and its esters, $N^G$-monomethyl-L-arginine, 2-iminopipperidines and other 2-iminoazaheterocycles.

Other possible anti-oxidants that the derivative may contain are those that have one or more thiol functions (—SH) in either reduced or non-reduced form such as glutathione, lipoic acid, thioglycolic acid and other sulfhydryl compounds. The levels of sulfhydryl anti-oxidants should not exceed 0.5% for cosmetic uses of the composition, but may be higher for pharmaceutical uses as dictated by the considerations of efficacy. The composition may also include inorganic anti-oxidants, such as sulfites, bisulfites, metabisulfites or other inorganic salts and acids containing sulfur in oxidation state +4. The preferred level of inorganic sulfur-containing anti-oxidants is about 0.01 to about 0.5 with the most preferred level about 0.1% to about 0.4 by weight percent.

The L-ascorbic acid derivative may be used with about 0.025% to about 5%, preferably about 0.5 to about 3 weight percent, and most preferably about 0.5 to about 1 weight percent, of compounds known to be electron spin-traps, such as nitrones, N-tert-butylnitrone and α-[4-pyridyl 1-oxide]-N-tertbutyl nitrone or other compounds known to form free radicals with half-life time of more than 1 min.

About 0.001 to about 50 weight percent of the L-ascorbic acid derivative can also be used in compositions that contain insect repellents such as aliphatic, cyclic or aromatic amides, citronella oil, terpineol, cineole, neem oil and terephthalic acid and its esters. Other suitable insect repellents can be found in Technical Bulletin No. 1549 from the U.S. Department of Agriculture or in their Agricultural Handbook Nos. 69, 340 and 461.

The about 0.001 to about 50 weight percent L-ascorbic acid derivative is also suitable for topical compositions that contain skin cooling compounds such as, for example, menthol, menthyl glycerol, asymmetrical carbonates, thiocarbonates and urethanes, N-substituted carboxamides, ureas or phosphine oxides such as described in *J. Cosmet, Cham.*, vol. 29, p. 185 (1978), menthyl lactate and menthone glycerine acetal.

The L-ascorbic acid derivative can be used with other cosmetic and pharmaceutical actives and exponents, such as, for example, antifungals, antiallergenic agents, depigmenting agents, antiinflammatory agents, anesthetics, surfactants, moisturizers, exfolients, stabilizers, antiseptics, lubricants, chelating agents and skin penetration enhancers. When used with these ingredients, the L-ascorbic acid derivative may provide additional dermatological and/or cosmetic benefits.

The L-ascorbic acid derivative can also be formulated in the form of micro-emulsions. The micro-emulsion system would typically contain an effective amount of the L-ascorbic acid derivative, up to 18% of a hydrocarbon, up to 40% of an oil, up to 25% of a fatty alcohol, up to 30% of a non-ionic surfactant, and up to 30% of water.

The L-ascorbic acid derivative is suitable and convenient for use in topical products formulated in the form of oil-in-water or water-in-oil emulsions, ointments, sticks, sprays, tapes, patches, as multiphase emulsion compositions, such as water-in-oil-in-water type as disclosed in U.S. Pat. No. 4,254,105, incorporated herein by reference. The L-ascorbic acid derivative can also be formulated as triple emulsions of the oil-in-water-silicone fluid type as disclosed in U.S. Pat. No. 4,960,764 incorporated herein by reference.

The L-ascorbic acid derivative can also be made as a liposomal formulation, for example, according to the methods described in Mezei, *J. Pharmaceut. Pharmacol.*, vol. 34, pp. 473–474 (1982) or modification thereof. In such compositions, droplets of the L-ascorbic acid derivative can be entrapped inside the liposomal vesicles and then incorporated into the final formula with the shell of the liposome being a phospholipid but which can be replaced with other suitable lipids (e.g., skin lipids). The liposomes can then be added to any carrier system described above according, for example, to the preparation modes, uses and compositions of topical liposomes as described in Mezei, *Topics in Pharmaceutical Sciences*, Breimer et al. Eds., pp. 345–358, Elsevier Science Publishers BV, New York (1985), incorporated herein by reference, or according to the reverse-phase evaporation method described in Szoka et al., *Proc. Nat. Acad. Sciences*, vol. 75, pp. 4194–4198 (1978), and also in Diploses et al., *J. Soc. Cosmetic Chemists*, vol. 43, pp. 93–100 (1992), all incorporated herein by reference.

The L-ascorbic acid derivative can also be entrapped in polymeric vesicles with a shell consisting of a suitable polymeric material, such as gelatin, cross-linked gelatin, polyamide, poylacrylates and the like. These vehicles can then be incorporated into any composition set forth herein.

The general activity and mildness to skin can also be enhanced by neutralization to pH 3.5 to 8.0, most preferably from pH 3.7 to 5.6, with one or more amphoteric and pseudoamphoteric compounds selected from a group including, but not limited to, glycine, alanine, valine, serine, thionine, methionine, leucine, asparagine, histidine, glutamic acid, glutamine, lysine, cystine, cystein, tryptophan, serine, phenylalanine, citrulline, creatine, proline, 3- or 4-hydroxyproline, 5-hydroxylysine, ornithine and its derivatives, 3-aminopropanoic acid and other aminocarboxylic acids, canavanine, canaline, homoarginine, taurine, aminoaldonic acids and aminosugars, aminouronic acid, aminoaldaric acid, deacetylated hyaluronic acid, hyalobiuronic acid, chondrosine, desulfated heparin, neuraminic or sialic acid, methionine sulfone, glycylglycine, chondroitin, D,L-sphingosine, sphingomyelin, ophidine, glucagon, homocarnosine, phosphatidyl serine, cocoamphoglycine, phosphatidyl ethanolamine, cysteine-sulfinic acid, glutathione, amphoteric inorganic oxides, polyamidoamines, polyamidoamines-based dendrimers, sodium hydroxymethylglycinate and polyethylene amine.

When about 0.001 to about 20 of L-ascorbic acid derivative is used with certain chelating agents, the utility and mildness of the composition can also be enhanced. The chelating agents should be from about 0.01 to about 25, more preferably from about 0.5 to about 10, and most preferably from about 1 to about 5 weight percent. Suitable examples of chelating agents include those that have a high affinity for zinc, calcium, magnesium, iron and/or copper ions, such as ethylene-diamine-tetra-acetic acid (ethylenedioxy)-diethylene-dinitrilo-tetra-acetic acid, salicylaldoxime, quinolinol, diaminocyclohexane-tetra-acetic acid, diethylene-triaminopenta-acetic acid, dimethylglyoxime, benzoin oxime, triethylenetetramine, desferrioxamine or mixtures thereof.

The L-ascorbic acid derivative has been unexpectedly and surprisingly found to be useful as active agent in topical preparations for treating signs of dermatological aging, both photoaging and intrinsic aging, including skin wrinkles such as fine wrinkling in the eye areas or "crows feet," or fine wrinkles around the mouth area, irregular pigmentation, sallowness, loss of skin resilience and elasticity. The present compound is also useful for treating disorders associated with the nails, cuticles and hair such as ingrown hair, folliculitis and *Pseudofolliculitis barbae*. It has been discovered that the present compounds soften hair and promotes the elimination of hair ingrowths, and are particularly useful for shaving.

The L-ascorbic acid derivative also enhances protection against UV provided by known sunscreen formulations.

The present invention also relates to a method for coupling a molecule of L-ascorbic acid to a molecule of cholesterol. The coupling preferably occurs through a bioreversible phosphate linkage at position 2 or 3 on the ascorbyl group and position 3' on the cholesteryl moiety.

Resulting compositions are also contemplated by this invention.

Formula I was formed by preparing the conjugated 3'-(L-ascorbyl-2-o-phosphoryl)-cholesterol by dissolving cholesterol at −10 degrees C. in dry diethyl ether (dried with 4A molecular sieves) containing 1.0 equivalent of triethylamine as a base. Phosphorous oxichloride (1.0 equivalent) was added to provide cholesteryl phosphorodichloridate.

The melting point of the cholesteryl phosphorodichloridate was measured as 121–122 degrees C. and infrared (KBr pellet) analysis showed P=O absorption at 1298 wavelengths and P—O—C absorption at 1019 wavelengths, with no hydroxyl absorption. Cholesteryl phosphorodichloridate was subsequently reacted for 3 hours at room temperature with 5,6-isopropylidene-L-ascorbic acid in tetrahydrofuran containing 1.0 equivalent of triethylamine. This reaction yielded a mixture of cholesteryl 5,6isopropylidene-2-phosphorochloridate L-ascorbic acid and its isomer cholesteryl 5,6-isopropylidene-3-phosphorochloridate L-ascorbic acid.

The isomeric moisture was hydrolyzed in an aqueous solution of THF and stirred for several hours at room temperature with Amberlyst-15, a strongly acidic sulfonic acid ion exchange resin. THF and water were then removed. The final product, 3'-(L-ascorbyl-2-o-phosphoryl)-cholesterol, was extracted with ethyl acetate and neutralized with an KOH equivalent. The resulting solution was lyophilized to obtain the monopotassium salt form.

This novel method permits covalent and bioreversible coupling of cholesterol with L-ascorbic acid resulting in the stabilization of ascorbic acid, and increased bioavailability for ascorbic acid and cholesterol.

The compounds of the present invention are generally synthesized by reacting cholesterol with a halogenophosphorelating agent, (b) coupling the resulting product with 5,6-hydroxyl protected L-ascorbic acid, (c) hydrolyzing the product with water, (d) stripping the protective group with an acidic resin and (e) purifying the product with lyophilization and recrystalization. The derivative is stable in solution, exhibits anti-oxidant activity and stimulates production of collagen in fibroblasts.

EXAMPLE 1

Preparation of Phosphodiester Acid and its Mono Potassium Salt

Cholesteryl phosphodichloridate was synthesized using the following procedure. A 250 ml two neck 19/22 ST round bottom flask was selected for the reaction. It included a serum cap (with nitrogen inlet needle), a stirring bar and a 19/22 to 24/40 ST 125 ml dropping funnel equipped with a side arm. This apparatus was flame dried and cooled under a nitrogen sweep. The dropping funnel was charged with 4.64 grams (12 mmole) of Sigma 99+% cholesterol, 75 ml of ether (dried over activated 4A molecular sieves) and 1.214 grams (12 mole, 1.672 ml) of dry (over KOH) triethylamine.

The flask was charged with 28 ml of dry ether and 1.84 grams (12 mole, 1.118 ml) of phosphorous oxychloride and cooled in an ice/methanol (−10 degrees C.) bath. Ether containing the cholesterol-triethylamine was added dropwise at a brisk rate over a period of 20 to 30 minutes. The solution was warmed to room temperature and stirred for 2.5 hours.

Precipitated solids were filtered off on a Buchner funnel and washed three times in water with thorough stirring. Air was introduced through the Buchner funnel until all of the ether in the filtrate evaporated. Solid precipitate was then removed by filtration through a second Buchner funnel and cholesteryl phosphodichloridate was dried in a vacuum desiccator over phosphorous pentoxide. This experiment yielded 3.90 grams (65%) of first crop solid, mp 121–122 degrees C. and 1.74 grams (29%) of second crop material, mp 117–118 degrees C. IR analysis (KBr pellet) showed (C—H) absorption at 2947 wavelengths, (=C—R) absorption at 2878 wavelengths, (C=C) absorption at 1466 wavelengths, (P=O) absorption at 1298 wavelengths and (P—O—C) absorption at 1019 wavelengths.

Ascorbic cholesteryl phosphodiester chloridate was synthesized following the procedure as outlined below.

A 50 ml three neck 19/22 ST round bottom flask fitted with a stirring bar, serum cap, nitrogen inlet needle and 50 ml dropping funnel was selected for this experiment. This apparatus was flame dried and cooled under a nitrogen sweep. The dropping funnel was charged with 503 mg (1 mmole of cholesteryl phosphorodichloridate (mp 122 degrees C.) and 15 ml of dry THF, and the mixture was cooled in an ice/methanol bath (−10 degrees C.). To the cooled mixture was added 216 mg (1 mmole) of Sigma 5,6-isopropylidene-L-ascorbic acid, 15 ml of dry THF and 0.14 ml (101 mg, 1 mmole) of dry (KOH) triethylamine. After addition, the mixture was warmed to room temperature and stirred for 3 hours.

A TLC (25% methanol/toluene) analysis indicated the reaction was complete. It also suggested that the product was a mixture of 2-0 and 3-0 regioisomers. The precipitated triethylamine hydrochloride was removed by filtration through fluted paper. THF was removed by rotary evaporation to provide 0.66 grams (97%) of crude crystalline ascorbic cholesteryl phosphodiester chloridate.

Ascorbic cholesteryl phosphodiester acid was prepared utilizing the following procedure. Crude ascorbic cholesteryl phosphodiester chloridate (6.76 grams, 9.9 mmole) in 60 ml of THF was combined with 30 ml of water and 20 grams of wet Amberlyst-15 that had been rinsed in water three times. The resulting mixture was stirred vigorously at room temperature for 55 hours. Amberlyst-15 was removed by filtration through fluted paper and was rinsed once with 20 ml of 1:1 THF/water. Most of the THF was removed in a stream of nitrogen to provide 53 ml of a thick cloudy aqueous suspension.

Fifty three (53) ml of THF was added to the suspension to yield 106 ml of 1:1 THF/water solution of crude phosphodiester acid that was nearly clear. Phosphodiester acid was purified by adding the 1:1 THF/water solution to a column of C-18 reverse phase silica gel (472 grams) and eluting with 1:1 THF/water. THF was removed in a stream of nitrogen to give 215 ml of purified phosphodiester acid in aqueous suspension. The projected total yield was 1.74 grams (28%), and the actual isolated yield was 1.84 grams (30%). Reverse phase HPLC analysis indicated 90% purity.

Ascorbic cholesteryl phosphodiester diacid mono potassium salt was made by first treating a 1% aqueous solution of the diacid with one equivalent of a standardized potassium hydroxide solution and subsequent lyophilization. The phosphodiester diacid (579 mg, 0.927 mmole) was dissolved in 57.9 ml of water and treated with 9.44 ml of 0.0986 N potassium hydroxide solution (0.931 mmole). The neutralized solution was then lyophilized to remove water and yield 603 mg (98%) of mono potassium salt as a fluffy white solid.

EXAMPLE 2

Purification by Reverse Phase C-18 Chromatography

Reverse Phase C-18 silica gel was prepared on a 1 kg scale according to Evans, Chromatographia, Vol. 13, pages 5–10 (1980). Purification of the phosphodiester acid to a level of 90% was achieved at a 90:1 load ratio using 1:1 THF/water, followed by THF removal in a stream of nitrogen and water removal by lyophilization. Investigation of other solvent systems by reverse phase thin layer chromatography has good potential to (i) improve the level of purity, (ii) identify an effective separation medium that could be removed by rotary evaporation, and (iii) allow the use of a lower load ratio. Since the reverse phase C-18 silica gel is reusable, the method has good potential for purification up to 1000 grams.

Solvent systems that are suitable include THF/methanol, THF/ethanol, THF/isopropanol, dioxane/methanol, dioxane/ethanol, dioxane/isopropanol, ether/methanol, ether/ethanol, ether/isopropanol, ethyl acetate/methanol, ethyl acetate/ethanol, ethyl acetate/isopropanol, methylene chloride/ethanol, methylene chloride/methanol, methylene chloride/isopropanol, DME/methanol, DME/ethanol and DME/isopropanol.

Conjugation with cholesterol converts the polar ascorbic acid to a more non-polar lipophilic ascorbyl group that is readily absorbed through the stratum corneum. Once past the stratum corneum, the absorbed compound is able to effect underlying fibroblasts. The benefits of bioreversed ascorbic acid and cholesterol have been previously explained. Surprisingly, the conjugated compound itself stimulates collagen synthesis which enhances the integrity, elasticity and resiliency of skin. Additional details are provided in Example 3.

EXAMPLE 3

Fibroblast Studies

This example summarizes a study in which the ability of 3'-(L-ascorbyl-2-o-phosphoryl)-cholesterol to stimulate collagen production in cultured human skin fibroblasts is demonstrated. An art-recognized [$^3$H]-Proline Incorporation Assay was performed with different doses of 3'-(L-ascorbyl-2-o-phosphoryl)-cholesterol. Juva, *Anal. Biochem.*, Vol. 15, pages 77–83 (1966); Booth, *Biochem. Biophys. Acta*, Vol. 675, pages 117–122 (1981).

Fibroblasts were incubated with 0 μg/ml, 11.3 μg/ml, 22.5 μg/ml and 45 μg/ml of 3'-(L-ascorbyl-2-o-phosphoryl)-cholesterol for a total of 48 hours. After the first 24 hours [$^3$H]-labeled proline was added to the culture. Following the second 24 hour period, the cells are harvested and prepared for the collagen biosynthesis assay.

Protease inhibitors are added to prevent degradation of collagen and other proteins. The cell layer is scraped into a solution containing 0.4 M NaCl and 0.01 M Tris (pH 7.5). Extracts are sonicated to disrupt cell membranes. Separate volumes of the cell-containing solution (1 ml each) are dialyzed overnight against several changes of deionized water. The retentate is removed from dialysis and hydrolyzed in 6 N hydrochloric acid at 120 degrees C. overnight. The assay is performed using an oxidation process with 2 M chloramine-T. Samples are analyzed for radioactive counts, which represent the amount of newly synthesized [$^3$H]-hydroxyproline—an index for new collagen synthesis.

It was discovered that 3'-(L-ascorbyl-2-o-phosphoryl)-cholesterol increased production of new collagen by human skin fibroblasts in a dose dependent manner as illustrated by FIG. 1.

Various modifications and alterations to the present invention may be appreciated based on a review of this disclosure. These changes and additions are intended to be within the scope and spirit of this invention as defined by the following claims.

What is claimed is:

1. A topical formula suitable only for topical application comprising a vehicle and from about 0.001 to about 99 weight percent of a compound selected from the group consisting of 3'-(L-ascorbyl-2-o-phosphoryl)-cholesterol, 3'-(L-ascorbyl-3-o-phosphoryl)-cholesterol, an isomer thereof, a salt thereof, and a mixture thereof.

2. The topical formula of claim 1, wherein said salt is selected from the group consisting of ammonium, calcium, lithium, potassium, sodium, an organic amine and a mixture thereof.

3. The topical formula of claim 1, wherein said compound is selected form the group consisting of 3'-(L-ascorbyl-2-o-phosphoryl)-cholesterol, 3'-(L-ascorbyl-3-o-phosphoryl)-cholesterol, and a mixture thereof.

4. The topical formula of claim 1, wherein said vehicle is selected from the group consisting of a lotion, cream and gel.

5. The topical formula of claim 1, wherein said compound is about 0.05 to about 50 weight percent.

6. The topical formula of claim 1, wherein said compound is about 0.10 to about 20 weight percent.

7. The topical formula of claim 1, wherein said compound is about 1.0 to about 10 weight percent.

8. The topical formula of claim 4, wherein the pH of the topical formula is adjusted to physiologically acceptable levels with sufficient amounts of a compound selected from the group consisting of ammonium hydroxide, calcium hydroxide, lithium hydroxide, potassium hydroxide, sodium hydroxide, ethanolamine, diethanolamine and urea.

9. A lotion comprising about 0.10 to about 20.0 weight percent of a compound selected from the group consisting of 3'-(L-ascorbyl-2-o-phosphoryl)-cholesterol, isomers thereof and salts thereof, and water.

10. The lotion of claim 9, further comprising from about 0.001 to about 1.5 weight percent thickening agent.

11. The lotion of claim 10, wherein said thickening agent is selected from the group consisting of xanthan gum, hydroxyethyl cellulose or a combination thereof.

12. A topical formula comprising:
   (a) about 0.10 to about 20.0 weight percent of a compound selected from the group consisting of 3'-(L-ascorbyl-2-o-phosphoryl)-cholesterol, isomers thereof and salts thereof;
   (b) about 0.5 to about 6.0 weight percent emollient;
   (c) about 4.8 to about 14.5 weight percent emulsifier; and,
   (d) about 0.5 to about 1.4 weight percent thickening agent.

13. The topical formula of claim 12, further comprising about 0.35 to about 0.45 weight percent preservative.

14. The topical formula of claim 13, wherein the emollient is glycerin; and wherein the emulsifier is a combination of about 2.0 to about 8.0 weight percent of propylene glycol decapitate, about 1.8 to about 4.0 weight percent of Peg 40 Stearate, and about 1.0 to about 2.5 weight percent of Steareth-2.

15. The topical formula of claim 14, wherein the thickening agent is about 0.25 to about 0.70 weight percent of xanthan gum and about 0.25 to about 0.70 weight percent of hydroxyethyl cellulose.

16. The topical formula of claim 14, wherein the preservative is about 0.15 to about 0.20 weight percent of an EDTA salt, and about 0.20 to about 0.25 weight percent of methylparaben.

17. A topical cream comprising:
   about 0.10 to about 20.0 weight percent of a compound selected from the group consisting of 3'-(L-ascorbyl-2-o-phosphoryl)-cholesterol, isomers thereof and salts thereof;

about 0.1 to about 1.2 weight percent of a thickening agent;

about 0.1 to about 15 weight percent of an emulsifier; and, water.

18. The topical cream of claim 17, further comprising up to about 1 weight percent of fragrance.

19. A topical cream comprising:
(a) about 0.1 to about 20.0 weight percent of a compound is selected from the group consisting of 3'-(L-ascorbyl-2-o-phosphoryl)-cholesterol, isomers thereof and salts thereof;
(b) about 0.5 to about 4.0 weight percent emollient;
(c) about 2.0 to about 6.0 weight percent emollient/humectant;
(d) about 4.5 to about 11.0 weight percent emulsifier;
(e) about 0.5 to about 1.2 weight percent thickening agent; and,
(f) about 0.15 to about 0.2 weight percent preservative.

20. The topical cream of claim 19, wherein the emollient is glycerin; and wherein the emollient/humectant is propylene glycol decapitate; and wherein the emulsifier is about 1.8 to about 3.0 weight percent Steareth-20, about 0.8 to about 2.0 weight percent Steareth-2, about 1.0 to about 2.5 weight percent cetyl alcohol, and about 0.9 to about 3.5 weight percent glycerol mono-stearate; and wherein the thickening agent is about 0.25 to about 0.6 weight percent xanthan gum and about 0.25 to about 0.6 weight percent hydroxyethyl cellulose.

21. The topical cream of claim 20, wherein the preservative is an EDTA salt.

22. A topical gel comprising:
about 0.10 to about 20 weight percent of a compound is selected from the group consisting of 3'-(L-ascorbyl-2-o-phosphoryl)-cholesterol, isomers thereof and salts thereof;
about 0.30 to about 2.0 weight percent thickening agent; and,
water.

23. A topical gel comprising:
about 0.10 to about 20.0 weight percent of a compound is selected from the group consisting of 3'-(L-ascorbyl-2-o-phosphoryl)-cholesterol, isomers thereof and salts thereof;
about 2.0 to about 6.0 weight percent emollient/humectant;
about 0.4 to about 1.5 weight percent thickening agent; and,
about 0.35 to about 0.45 weight percent preservative.

24. The topical gel of claim 23, wherein the emollient/humectant is propylene glycol; wherein the preservative is about 0.20 to about 0.25 weight percent methylparaben, and about 0.15 to about 0.20 weight percent an EDTA salt; and wherein the thickening agent is selected from a group consisting of xanthan gum, hydroxypropyl cellulose, hydroxyethyl cellulose, carbopol and gum acacia, polyacrylamide isoparaffin emulsion, vee-gum, magnesium aluminum silicate and a mixture thereof.

25. The topical gel of claim 24, wherein said thickening agent is hydroxyethyl cellulose.

26. The topical formula of claim 1, further comprising an alpha-hydroxy acid, wherein the topical formula comprises about 0.001 wt % to about 10 wt % of said compound.

27. The topical formula of claim 1, further comprising a retinoid, wherein the topical formula comprises from about 0.001 wt % to about 10 wt % of said compound.

28. The topical formula of claim 27, wherein said retinoid is retinol.

29. The topical formula of claim 1, further comprising a sunscreen, wherein the topical formula comprises from about 0.001 wt % to about 25 wt % of said compound.

30. The topical formula of claim 29, wherein said sunscreen is selected from the group consisting of a methyl cinnamic acid, an octyl cinnamic acid, a 2-ethylhexyl cinnamic acid and derivatives thereof, a benzyl cinnamic acid and derivatives thereof, alphaphenyl cinnamonitrile, butyl cinnamoyl pyruvate, titanium dioxide, zinc oxide, benzylidene camphor, an anthranilate, a naphtholsulphonate and a mixture thereof.

31. The topical formula of claim 1, further comprising an antioxidant.

32. The topical formula of claim 31, wherein said antioxidant is selected from the group consisting of sulfites, bisulfites, metabisulfites, and a mixture thereof.

33. The topical formula of claim 32, wherein said antioxidant is a sulfite.

34. The topical formula of claim 1, further comprising a hormonal compound selected from the group consisting of estriol, estradiol, estrone, conjugated estrogens and a mixture thereof,
wherein the topical formula comprises about 0.001 wt % to about 10 wt % of said compound.

35. The topical formula of claim 1, further comprising a self-tanning agent, wherein the topical formula comprises from about 0.001 wt % to about 20 wt % of said compound.

36. The topical formula of claim 35, wherein said self-tanning agent is selected from the group consisting of dihydroxyacetone, lawsone and a mixture thereof.

37. The topical formula of claim 1, wherein said vehicle further comprises at least one component selected from the group consisting of a fragrance, an emulsifier, a thickening agent and an emollient.

38. A method of softening hair, promoting the elimination of hair ingrowths, treating folliculitis or pseudofolliculitis barbae, the method comprising the step of applying the topical formula of claim 1 to said hair or to the base of said hair.

39. The topical formula of claim 1, further comprising a skin cooling agent selected from the group consisting of menthol, menthyl glycerol, an asymmetrical carbonate, a thiocarbonate, an urethane, a N-substituted carboxamide, an urea, a phosphine oxide, menthyl lactate, menthone glycerin acetal, and a mixture thereof, wherein the topical formula comprises from about 0.001 to about 50 weight percent of said compound.

* * * * *